(12) United States Patent
Hickman

(10) Patent No.: US 11,617,873 B1
(45) Date of Patent: Apr. 4, 2023

(54) CATHETER CONNECTION SECURING QUICK RELEASE

(71) Applicant: Chuck Andrew Hickman, Modesto, CA (US)

(72) Inventor: Chuck Andrew Hickman, Modesto, CA (US)

(*) Notice: Subject to any disclaimer, the term of this patent is extended or adjusted under 35 U.S.C. 154(b) by 0 days.

(21) Appl. No.: 18/056,297

(22) Filed: Nov. 17, 2022

Related U.S. Application Data

(63) Continuation-in-part of application No. 17/661,335, filed on Apr. 29, 2022.

(51) Int. Cl.
| | |
|---|---|
| *A61M 25/16* | (2006.01) |
| *A61M 25/18* | (2006.01) |
| *A61M 39/00* | (2006.01) |
| *A61M 39/10* | (2006.01) |

(52) U.S. Cl.
CPC ..... *A61M 39/10* (2013.01); *A61M 2039/1027* (2013.01)

(58) Field of Classification Search
CPC ...... A61M 2025/024; A61M 2025/028; A61M 2025/0246; A61M 25/02; A61M 25/0021; A61M 2205/586
See application file for complete search history.

(56) References Cited

U.S. PATENT DOCUMENTS

| | | | |
|---|---|---|---|
| 4,896,465 A * | 1/1990 | Rhodes | A61M 5/1418 |
| | | | 451/523 |
| 5,531,695 A | 7/1996 | Swisher | |
| 2002/0007538 A1 * | 1/2002 | Bourgerie | A01K 97/08 |
| | | | 24/517 |
| 2008/0125718 A1 | 5/2008 | Tsuchiya et al. | |
| 2014/0324024 A1 | 10/2014 | Tejani | |
| 2015/0308598 A1 | 10/2015 | Lewis et al. | |
| 2016/0053926 A1 | 2/2016 | Whitaker | |

(Continued)

FOREIGN PATENT DOCUMENTS

| | | |
|---|---|---|
| CN | 114256717 A | 3/2022 |
| EP | 847284 A1 | 6/1998 |

OTHER PUBLICATIONS

Amaral CA, Amaral TLM, Monteiro GTR, Vasconcellos MTL, Portela MC, Hand grip strength: Reference values for adults and elderly people of Rio Branco, Acre, Brazil, article, retrieved on Nov. 15, 2022, PLoS ONE, Brazil.

*Primary Examiner* — Rebecca E Eisenberg
(74) *Attorney, Agent, or Firm* — Carson Patents®; Gregory D Carson

(57) ABSTRACT

The ergonomic catheter bag quick release is an apparatus in the form of a catheter tubing grip shell for creating a secure connection between a catheter and a catheter collection bag comprising a rigid catheter sleeve having a lever along its length to enable a substantial reduction in strength required to create a positive locked gripping connection over said connection between a catheter and a catheter collection bag. It is a catheter tubing grip shell with an ergonomically shaped lever that enables elderly and strength weakened patients to be able to secure the connection between a catheter and a catheter collection bag with far less than normal adult grip strength. It can optionally be fitted with a compressible sleeve to enable the creation of a water-leak resistant connection between a catheter and a catheter collection bag.

6 Claims, 1 Drawing Sheet

(56) References Cited

U.S. PATENT DOCUMENTS

2020/0254158 A1\* 8/2020 Burkin .................. A61M 1/682
2020/0254221 A1    8/2020 Burkin
2020/0282182 A1\* 9/2020 Blackman ............. A61M 25/02
2021/0268255 A1\* 9/2021 O'Neil ............... A61M 39/1011

\* cited by examiner

CATHETER CONNECTION SECURING QUICK RELEASE

CROSS REFERENCE TO RELATED APPLICATIONS

This continuation in part application claims the benefit under 35 U.S.C. § 119(e) of U.S. patent application Ser. No. 17/249,870, filed Mar. 17, 2021 the disclosure of which is incorporated by reference herein, Continuation In Part application Ser. No. 17/449,259, filed Sep. 29, 2021 the disclosure of which is incorporated by reference herein, and Continuation In Part application Ser. No. 17/661,335, filed Apr. 29, 2022 the disclosure of which is incorporated by reference herein.

BACKGROUND OF THE INVENTION

Technical Field

This invention relates generally to a catheter connection securing device in the form of an externally applied snap-to-close clam shell (sleeve) with thumb tab locking mechanism to enable securing a connection of a catheter collection bag to a catheter.

This invention relates specifically to a catheter connection securing device that enables maintaining a connection between a catheter collection bag and a catheter. This invention relates specifically to a catheter connection securing device that requires minimal or little grip strength or motion stability to positively and easily secure the connection between a catheter collection bag and a catheter. This invention relates specifically to a catheter connection securing device that enables maintaining a leak-resistant or leak-proof connection between a catheter collection bag and a catheter.

This invention relates specifically to an ergonomic catheter connection securing device that enables maintaining a connection between a catheter collection bag and a catheter. This invention relates specifically to an ergonomic catheter connection securing device that requires minimal or little grip strength or motion stability to positively and easily secure the connection between a catheter collection bag and a catheter. This invention relates specifically to an ergonomic catheter connection securing device that enables maintaining a leak-resistant or leak-proof connection between a catheter collection bag and a catheter.

Background Art

Today, the connection and disconnection of a catheter to a catheter collection bag is a matter of pushing a flexible hose connection over a rigid hose end hopefully far enough to both be water-tight and stay in place. The pushing together of a flexible and rigid end to achieve a water-tight connection that will stay in place requires average human grip strength and stability (lack of shakiness in the fingers, hands, wrists, and arms).

Average grip strength is commonly used in medical practices and therapies as an assessment and evaluation tool, and that grip strength drops with age and infirmity. It is known that adult male grip strength drops from about 42-44 kg at age 50 to about 25-28 kg at age 85, and adult female grip strength drops from about 25-28 kg at age 50 to about 15-17 kg at age 85. Many people who need and use a catheter are not healthy, well enough, or physically able to muster average human grip strength and stability and need an apparatus that would enable them to positively secure the connection between a catheter and a catheter collection bag.

Among the existing art available today that facilitates or enables a leak resistant or leak proof connection or disconnection and/or a disconnection resistant or locking connection for the connection between a catheter collection bag and a catheter, there are few options other than the existing flexible hose connection end over a rigid hose connection end. The available options include the existing end connections between a manufacturers catheters and collection bags, custom material and shaped versions thereof, and the wrapping of the connection with tape.

All available options require the application and use of average human grip strength and stability (lack of shakiness in the extremities). There are no options available for persons with less than average human grip strength or for persons with less than average stability. There are no options available that offer a combination of a leak resistant or leak proof connection and a disconnection resistant or locking connection to enable or facilitate the connection between a catheter collection bag and a catheter.

In light of the foregoing prior art, there is a need for an ergonomic device to surround the connection between a catheter and a catheter collection bag that requires less than normal strength to close and lock in order to provide a positive connection securing the connection between a catheter and a catheter collection bag with a simple thumb-lock tab.

Further, there is a need for an ergonomic device as above that offers a combination of a leak resistant or leak proof connection and a disconnection resistant or locking connection to connect a catheter collection bag and a catheter. And, there is a need for an ergonomic device that offers a combination of a leak resistant or leak proof connection and a disconnection resistant or locking connection to connect a catheter collection bag and a catheter that requires less than average human strength and/or less than average human hand stability to open and close enabling a disconnection and connection respectively.

BRIEF SUMMARY OF THE INVENTION

According to a first aspect of the invention, there is a catheter connection securing quick release apparatus in the form a hand held catheter tubing grip shell for securing an operable catheter to catheter bag connection comprising a cylindrical clam shell having an interior and a hinge along a first longitudinal edge comprising a top half shell comprising a first semi-circular opening in a first end opposing a second semi-circular opening in a second end having a top thumb-lock rail along a second longitudinal edge opposite said first longitudinal edge, a bottom half shell comprising a third semi-circular opening in a third end opposing a fourth semi-circular opening in a fourth end having a bottom thumb-lock rail along a third longitudinal edge opposite said first longitudinal edge aligned to mate with said top thumb-lock rail, a compressible lining covering said interior of said cylindrical clam shell, and a thumb-lock tab for a locking of said cylindrical clam shell having a knurled edge for sliding over said top thumb-lock rail and said bottom thumb-lock rail.

According to a second aspect of the invention, there is a catheter connection securing quick release apparatus in the form a hand held catheter tubing grip shell for securing an operable catheter to catheter bag connection wherein said cylindrical clam shell further comprises a length that is between six and eight centimeters.

According to a third aspect of the invention, there is a catheter connection securing quick release apparatus in the form a hand held catheter tubing grip shell for securing an operable catheter to catheter bag connection wherein said first semi-circular opening, said second semi-circular opening, said third semi-circular opening, and said fourth semi-circular opening further comprises a diameter that is between one and three centimeters.

According to a fourth aspect of the invention, there is a catheter connection securing quick release apparatus in the form a hand held catheter tubing grip shell for securing an operable catheter to catheter bag connection wherein said thumb-lock tab further comprises a knurled surface.

According to a fifth aspect of the invention, there is a catheter connection securing quick release apparatus in the form a hand held catheter tubing grip shell for securing an operable catheter to catheter bag connection further comprising a closing of said cylindrical clam shell wherein a resistance to closing is less than three kilograms.

According to a sixth aspect of the invention, there is a catheter connection securing quick release apparatus in the form a hand held catheter tubing grip shell for securing an operable catheter to catheter bag connection wherein said locking further comprises a force to close of less than one kilogram to move said thumb-lock tab.

According to a seventh aspect of the invention, there is a method of securing a connection between a catheter and collection bag using a hand held catheter tubing grip shell by nesting said connection inside said hand held catheter tubing grip shell, closing said hand held catheter tubing grip shell around said connection, and locking said hand held catheter tubing grip shell.

An advantage of the catheter connection securing quick release is the capability to create either of a positive secure and/or lockable connection between a catheter and catheter collection bag. A further advantage of the present invention is an apparatus that offers a combination of a leak resistant or leak proof connection to connect a catheter collection bag and a catheter that requires less than average human grip strength to open and close thus enabling a quick and easy disconnection and connection respectively.

The invention will now be described, by way of example only, with reference to the accompanying drawings in which:

DETAILED DESCRIPTION

Figure 1:
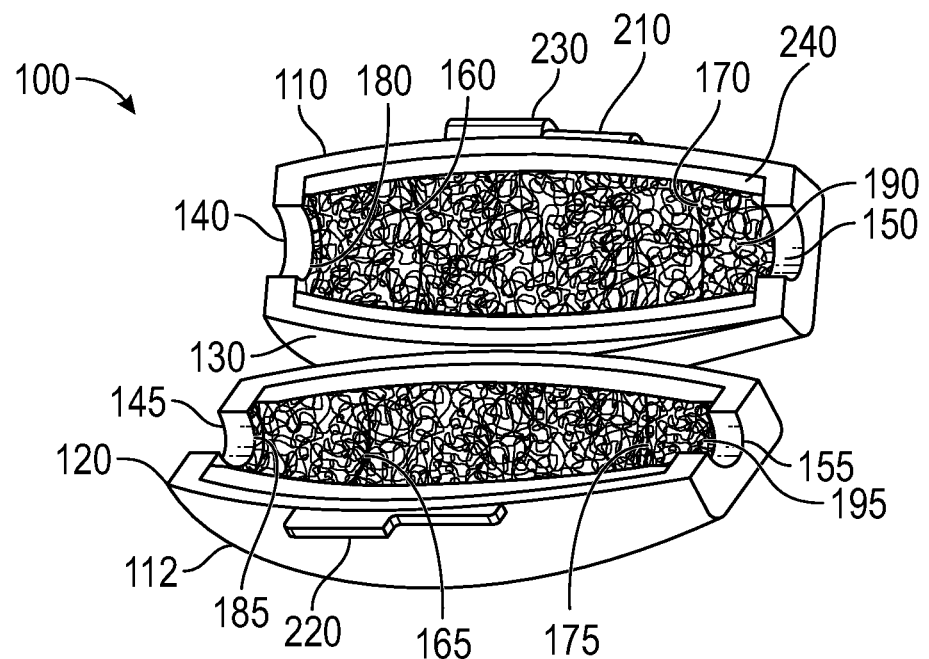
FIG. 1 is a perspective view of a catheter connection securing quick release according to the invention.

The detailed embodiments of the present invention are disclosed herein. The disclosed embodiments are merely exemplary of the invention, which may be embodied in various forms. The details disclosed herein are not to be interpreted as limiting, but merely as the basis for the claims and as a basis for teaching one skilled in the art how to make and use the invention.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Throughout this specification, the word "cylindania," or variations thereof, will be understood to imply the shape formed when a hollow tube is cut in half lengthwise (perpendicular the ends).

Throughout this specification, the phrase "catheter bag," or variations thereof, will be understood to imply the inclusion of the following: catheter collection bag, night bag, day bag, night collection bag, day collection bag, and urine collection bag.

The use of the phrase human grip strength refers to the average strength of the average person during a self-initiated and self-actuated crush grip, pinch grip, or support grip grabbing movement of the fingers, hands, wrists, forearms, elbows, upper arm, and shoulders while grabbing or gripping an object. Average human grip strength is known to decrease as people age and become infirm or disabled. The commonly known and accepted measurements of grip strength are used in this context. For example it is known that adult male grip strength drops from about 42-44 kg at age 50 to about 25-28 kg at age 85, and adult female grip strength drops from about 25-28 kg at age 50 to about 15-17 kg at age 85. Specifically, from Amaral et al., adult male grip strength drops from about 41.2 kg at ages 50-59 to about 25.7 kg at ages 80 and older, and adult female grip strength drops from about 24.2 kg at ages 50-57 to about 17.1 kg at ages 80 and older.

The use of the phrase human hand stability refers to the lack of movement of the fingers, hands, wrists, forearms, elbows, upper arm, and shoulders while moving. Average human hand stability is little to no shakiness of movement or motion. The sleeve (cylindrical tube shape) of the present invention is open for wrapping around a catheter to catheter bag connection enabling its application and use with less than average human hand stability.

Index of labelled elements and features in the figures, listed in numeric order by figure.

Figure 2:
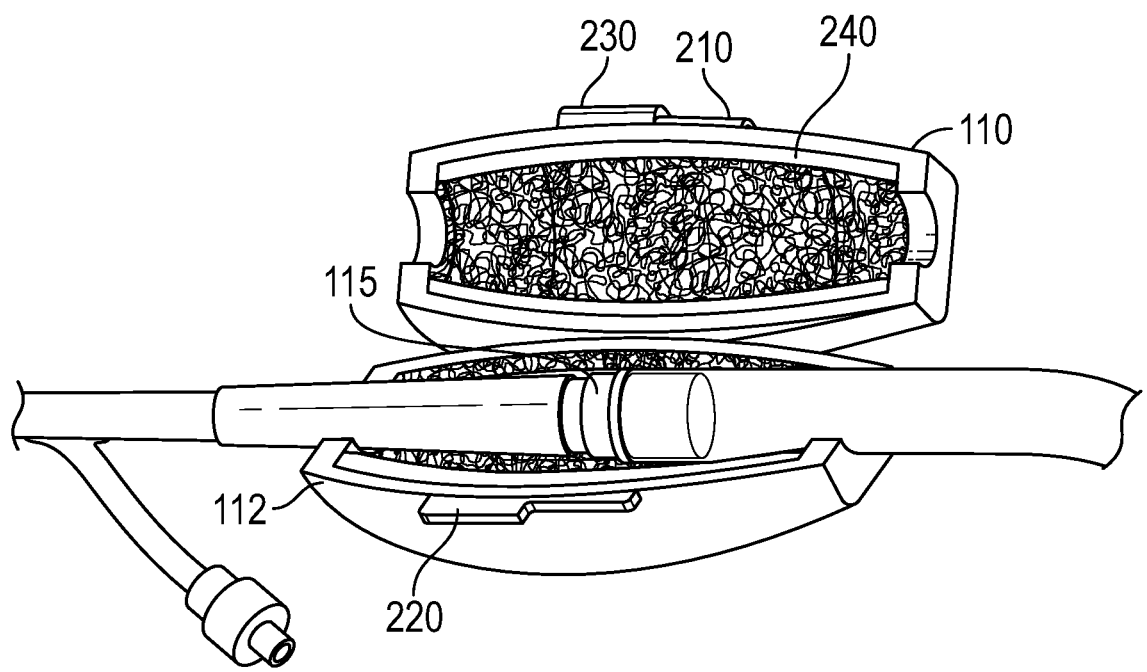
FIG. 2 is a perspective view of a catheter connection securing quick release showing a catheter and catheter collection bag being surrounded according to the invention.

Referring to the Figures, there is shown in FIGS. 1 and 2 the following features:

Element 100 is a cylindrical clam shell, catheter tubing grip shell, cylindania.
Element 110 is a catheter clam shell (sleeve) lid.
Element 112 is a catheter specimen tube insert notch.
Element 115 is a catheter tube end connection.
Element 120 is a catheter sleeve bottom.
Element 130 is a top longitudinal connecting edge (hinge)
Element 140 is a catheter sleeve lid sinistral opening.
Element 145 is a catheter sleeve bottom sinistral opening.
Element 150 is a catheter sleeve lid dextral opening.
Element 155 is a catheter sleeve bottom dextral opening.
Element 160 is a catheter sleeve lid sinistral cylindrical depression.
Element 165 is a catheter sleeve bottom sinistral cylindrical depression.

Element 170 is a catheter sleeve lid dextral cylindrical depression.
Element 175 is a catheter sleeve bottom dextral cylindrical depression.
Element 180 is a catheter sleeve lid sinistral radial depression.
Element 185 is a catheter sleeve bottom sinistral radial depression.
Element 190 is a catheter sleeve lid dextral radial depression.
Element 195 is a catheter sleeve bottom dextral radial depression.
Element 210 is a top thumb-lock rail.
Element 220 is a bottom thumb-lock rail.
Element 230 is a thumb-lock tab.
Element 240 is an inner lining.

The elements of the present invention may be made from any rigid or compressible material that can be fashioned into the shape and size required that result in the requirement of less than average strength to enable a leak resistant or leak proof connection and/or a disconnection resistant or locking connection to connect a catheter collection bag and a catheter to open and close enabling a disconnection and connection respectively. Embodiments known to function have been manufactured from several moldable and injectable plastics that are commonly known and available.

In an embodiment, the device of the present invention is made from two sleeves dimensioned having an axially oriented cavity with an internal dimension of not greater than that of a catheter tube 110, a catheter tube end connection 115, a catheter bag tube end 185 connection, a catheter bag tube 180.

In an embodiment, the device of the present invention is made from a single composite of two or more sleeves nested together and dimensioned having an axially oriented cavity with an internal dimension of not greater than that of a catheter tube 110, a catheter tube end connection 115, a catheter bag tube end 185 connection, a catheter bag tube 180. The thumb-lock tab 230 is made from the same material but as a separate element of the device, and is added to an otherwise completed cylindrical clam shell 100 to make a complete device according to the present invention.

The device of the present invention is used to create a positive secure connection and/or disconnection that comprises a resistant or locking connection to connect a catheter collection bag and a catheter that requires less than average human grip strength and/or less than average human hand stability to open and close enabling a disconnection and connection respectively.

The device of the present invention is used to create a combination of a leak resistant or leak proof connection and/or disconnection that comprises a resistant or locking connection to connect a catheter collection bag and a catheter that requires less than average human strength and/or less than average human hand stability to open and close enabling a disconnection and connection respectively.

In an embodiment, there is a catheter connection securing quick release apparatus for a creating a water-leak resistant connection between a catheter and a catheter bag comprising a rigid catheter sleeve 150 having a rigid catheter sleeve lid 155 along its length and a compressible catheter sleeve 160 dimensioned to wrap around said water-leak resistant connection between said catheter and said catheter bag and overfill said rigid catheter sleeve 150 wherein closing said lid 155 when said apparatus is positioned to surround a connection between said catheter and said catheter bag which enables a compression of said compressible catheter sleeve 160 which thereby enables said water-leak resistant connection between said catheter and said catheter bag.

In an embodiment, there is a catheter connection securing quick release apparatus wherein said water-leak resistant connection is instead a water-leak proof connection enabled by a compression of said compressible catheter sleeve 160.

In an embodiment, there is a catheter connection securing quick release apparatus wherein said water-leak resistance connection is also disconnection resistant enabled by a compression of said compressible catheter sleeve 160.

In an embodiment, there is a catheter connection securing quick release apparatus wherein said water-leak resistant connection is instead a water-leak proof and a disconnection resistant connection enabled by a compression of said compressible catheter sleeve 160.

In an embodiment, there is a catheter connection securing quick release apparatus wherein closing said lid requires less than average human grip strength to shut.

In an embodiment, there is a catheter connection securing quick release apparatus wherein closing said lid requires less than average human grip stability to shut.

In an embodiment, there is a catheter connection securing quick release apparatus wherein closing said lid requires less than average human grip strength and less than average human grip stability to shut.

In an embodiment, there is a catheter connection securing quick release apparatus wherein said compressible catheter sleeve has a plurality of elevated ridges oriented radially along its length.

In an embodiment, there is a catheter connection securing quick release apparatus wherein said compressible catheter sleeve has a plurality of elevated ridges oriented axially around its circumference.

In an embodiment, there is a catheter connection securing quick release apparatus wherein said rigid catheter sleeve 150 and said compressible catheter sleeve 160 are mated into a single sleeve further comprising a compressible material.

In an embodiment, there is a catheter connection securing quick release apparatus wherein said rigid catheter sleeve 150 and said compressible catheter sleeve 160 are mated into a single sleeve further comprising a compressible material having a plurality of elevated ridges oriented radially along its length.

In an embodiment, there is a catheter connection securing quick release apparatus wherein said rigid catheter sleeve 150 and said compressible catheter sleeve 160 are mated into a single sleeve further comprising a compressible material having a plurality of elevated ridges oriented axially around its circumference.

In an embodiment of the catheter connection securing quick release apparatus, there is a catheter tubing grip shell 100 comprising a top cylindania having a top longitudinal connecting edge and a top longitudinal lever edge having a rectangular top lever arm with a top thumb-lock rail distal to said top longitudinal connecting edge attached, a bottom cylindania having a bottom longitudinal connecting edge and a bottom longitudinal lever edge having a rectangular bottom lever arm with a bottom thumb-lock rail distal to said top longitudinal connecting edge attached, and a hinge connecting said top longitudinal connecting edge and said bottom longitudinal connecting edge.

In an embodiment of the catheter connection securing quick release apparatus, there is a catheter tubing grip shell comprising a top cylindania having a top longitudinal connecting edge and a top longitudinal lever edge having an ergonomically rounded rectangular top lever arm with a top thumb-lock rail distal to said top longitudinal connecting edge attached, a bottom cylindania having a bottom longitudinal connecting edge and a bottom longitudinal lever edge having an ergonomically rounded rectangular bottom lever arm with a top thumb-lock rail distal to said top longitudinal connecting edge attached, and a hinge connecting said top longitudinal connecting edge and said bottom longitudinal connecting edge.

In an alternate embodiment of the catheter connection securing quick release apparatus, there is a catheter tubing grip shell wherein said top lever arm is ergonomically rounded to nest in the palm of an open hand, and said bottom lever arm is ergonomically rounded to nest in the palm of an open hand.

In an alternate embodiment of the catheter connection securing quick release apparatus, there is a catheter tubing grip shell wherein said bottom lever arm further comprises a thumb-lock tab positioned on said bottom lever arm proximal to said bottom thumb-lock rail.

In an alternate embodiment of the catheter connection securing quick release apparatus, there is a catheter tubing grip shell further comprising a top cylindania compressible catheter sleeve nested in said top cylindania and said bottom cylindania compressible catheter sleeve nested in said bottom cylindania.

In an alternate embodiment of the catheter connection securing quick release apparatus, there is a catheter tubing grip shell further comprising a compressible sleeve split open along a longitudinal side nested in said top cylindania and said bottom cylindania.

In an alternate embodiment of the catheter connection securing quick release apparatus, there is a catheter tubing grip shell wherein said top cylindania compressible catheter sleeve has a plurality of elevated ridges oriented radially along its length and said bottom cylindania compressible catheter sleeve has a plurality of elevated ridges oriented radially along its length.

In an alternate embodiment of the catheter connection securing quick release apparatus, there is a catheter tubing grip shell wherein said top cylindania compressible catheter sleeve has a plurality of elevated ridges oriented axially around its circumference and said bottom cylindania compressible catheter sleeve has a plurality of elevated ridges oriented axially around its circumference.

In an alternate embodiment of the catheter connection securing quick release apparatus, there is a catheter tubing grip shell wherein said compressible catheter sleeve has a plurality of elevated ridges oriented radially along its length.

In an alternate embodiment of the catheter connection securing quick release apparatus, there is a catheter tubing grip shell wherein said compressible catheter sleeve has a plurality of elevated ridges oriented axially around its circumference.

In an embodiment of the catheter connection securing quick release apparatus, there is a catheter tubing grip shell comprising a top cylindania having a top longitudinal connecting edge and a top longitudinal lever edge having an ergonomically rounded rectangular top lever arm with a top thumb-lock rail distal to said top longitudinal connecting edge attached, a bottom cylindania having a bottom longitudinal connecting edge and a bottom longitudinal lever edge having an ergonomically rounded rectangular bottom lever arm with a bottom thumb-lock rail distal to said top longitudinal connecting edge attached, and a hinge connecting said top longitudinal connecting edge and said bottom longitudinal connecting edge.

In an embodiment of the catheter connection securing quick release apparatus, there is a method of securing a connection between a catheter and collection bag using a hand held catheter tubing grip shell by nesting said connection inside said hand held catheter tubing grip shell, closing said hand held catheter tubing grip shell around said connection, and locking said hand held catheter tubing grip shell.

In a preferred embodiment, there is a hand held catheter tubing grip shell for securing an operable catheter to catheter bag connection comprising a cylindrical clam shell having an interior and a hinge along a first longitudinal edge comprising a top half shell comprising a first semi-circular opening in a first end opposing a second semi-circular opening in a second end having a top thumb-lock rail along a second longitudinal edge opposite said first longitudinal edge, a bottom half shell comprising a third semi-circular opening in a third end opposing a fourth semi-circular opening in a fourth end having a bottom thumb-lock rail along a third longitudinal edge opposite said first longitudinal edge aligned to mate with said top thumb-lock rail, a compressible lining covering said interior of said cylindrical clam shell, and a thumb-lock tab for a locking of said cylindrical clam shell having a knurled edge for sliding over said top thumb-lock rail and said bottom thumb-lock rail.

The maximum dimensions of the completed device are limited for ergonomic purposes of facilitating gripping to surround, enclose, and operate the device of the present invention with a person's hand by the dimensions (length/distance measurements) of a person's hand. Ergonomic gripping feels comfortable in that it fits within the dimensions of a palm at maximum size and can completely enclosed by wrapping all of the fingers of the hand completely around the device so as to have all fingers be in contact at their tips with the palm of the hand.

Dimensioning the device to fit in a closed hand can be accomplished by any suitable means, but at least includes limiting the maximum circumference about any longitudinal point along the length of the closed device to less than the distance measurement from the base of the palm to the tip of the longest finger on the hand of a user so as to ensure a grip by the hand completely enclosing the device while closed over a catheter to catheter bag connection. There will be individually customizable preferences for size of the device limited only by the minimum size needed to enclose and encase a catheter to catheter bag connection all the way up to the largest circumference that a hand of a user could completely enclose by wrapping the finger(s) of the hand around the device and just barely being able to touch the palm of the hand with the finger tip of the finger wrapped around the device.

The known and accepted dimensions of the human palm vary up to as much as twenty centimeters by twenty centimeters. The average palm dimensions are less than ten centimeters by ten centimeters. In order to achieve ergonomic dimensions that fit comfortably in the palm, a cylindrical device can be up to about 70% of the size of the palm, but it is most easily handled at between 67% and about 33% of the size of the palm.

The maximum circumference of the device about a longitudinal point along its length should be limited to less than the reach distance of a finger wrapped around the device and able to make contact with the palm of the hand with the tip (end) of the finger. The maximum circumference of the device about its length is not limited like a point around its length because the devices length is ergonomically placed across the hand aligning with the base (attachment point of the finger to the hand) of the fingers where they connect with the palm. In other words, because the device is longer than it is wide the maximum circumference of the device about its length is not limited to the length of a hand from base of the palm to tip of the longest finger.

In an alternative embodiment, there is a hand held catheter tubing grip shell wherein said cylindrical clam shell further comprises a length that is between six and eight centimeters.

The amount of force needed to close the device is determined by the edge/hinge/connection between the top half and bottom half of the device. Ideally this amount of force is not greater than that force needed to fold the top half and the bottom half together along the edge/hinge/connection between them. This minimum force is determined by the weight of the device, the dimensions and configuration of the edge/hinge/connection between the top half and the bottom half, and the material used to manufacture the device.

The minimum force needed would be the force needed to move the weight (mass) of the top half towards the bottom half so as to close the shell and any force needed to overcome the resistance of the edge/hinge connection and any compressible material to move and close the device. With a minimum amount of force being between about 100 milligrams and 800 milligrams depending on the mass of the device and the compressibility of the lining material.

The maximum force needed to close the device that is most useful if less than average grip strength by as much as ninety percent. Sufficient resistance to offer a minimum amount of force needed for tactile feedback of a hand to be able to feel the object and control its motion and to close and lock the device helps ensure ergonomic comfort in hold and controlling while comfortably fitting the palm of a hand. A maximum force of less than three kilograms is best, and less force required is better.

Tensioning the hinge of the device is accomplished by constructing the hinge with materials that exhibit the needed strength characteristics so that the hinge is easy to move/fold by simply closing the hand around the device enabling the two halves (top and bottom) to be closed together. More flexible materials offer easier movement and rotation of the hinge, more rigid materials less. Other mechanical additions to the hinge or edge between the top and bottom halves of the device are accomplished by the addition of elements not shown in the figures, but that are used in the art of hinges to help close, keep closed, move, rotate, open, and keep open. Embodiments incorporating springs, levers, and other mechanical advantages are useful in versions of the present invention where in ease of movement, control, and use are contemplated ergonomically.

In an alternative embodiment, there is a hand held catheter tubing grip shell wherein said first semi-circular opening, said second semi-circular opening, said third semi-circular opening, and said fourth semi-circular opening further comprises a diameter that is between one and three centimeters.

The amount of force needed to close and/or open the locking tab by sliding the two elements together to lock or sliding the two elements apart to unlock is determined by the dimensions, configuration of shape and fit between elements, and the materials used to manufacture the device and the thumb-lock tab elements. The mass of the device, the distanced moved, and the compressibility of the lining materials are the usual determining factors for computing the forced needed.

The minimum amount of force needed to slid and lock the device is the amount of force needed to move the slidable element across the stationary element mating the thumb-lock rails and tab elements together and overcoming the force of friction needed to slid the locking elements into locked position. This amount of force is less than the force of movement of the thumb of a hand across a line, and is best implemented wherein the smallest amount of force needed to close and open the locking elements is minimized and easily accomplished within the capabilities of the thumbs motion across the palm for ergonomic purposes of competent control with a hand having as much as eighty percent less force than an average adult hand. A force to move and close/lock the thumb-lock tab 230 of less than one kilogram is best, and less force required is better.

In an alternative embodiment, there is a hand held catheter tubing grip shell wherein said thumb-lock tab further comprises a knurled surface.

In an alternative embodiment, there is a hand held catheter tubing grip shell further comprising a closing of said cylindrical clam shell wherein a resistance to closing is less than three kilograms.

In an alternative embodiment, there is a hand held catheter tubing grip shell wherein said locking further comprises a force to close of less than one kilogram to move said thumb-lock tab.

In a preferred embodiment of the present invention, there is a method of securing a connection between a catheter and collection bag using a hand held catheter tubing grip shell by nesting said connection inside said hand held catheter tubing grip shell, closing said hand held catheter tubing grip shell around said connection, and locking said hand held catheter tubing grip shell.

An advantage of the catheter connection securing quick release is the enablement of creating a connection between a catheter and a catheter collection bag that requires less than normal strength to close and lock in order to provide a positive connection securing the connection between a catheter and a catheter collection bag with a simple thumb-lock tab enabling elderly and weakened patents to more effectively manage their own care.

An advantage of the catheter connection securing quick release is the enablement of a leak resistant or leak proof connection to connect a catheter collection bag and a catheter that requires less than average human strength to open and close enabling a fast, simple, and easy to complete disconnection and connection respectively. An advantage of the catheter connection securing quick release is the enablement of a leak resistant or leak proof connection to connect a catheter collection bag and a catheter that requires less than average human hand stability to open and close enabling a fast, simple, and easy to complete disconnection and connection respectively.

An advantage of the catheter connection securing quick release is the enablement of a leak resistant or leak proof connection to connect a catheter collection bag and a catheter that requires less than average human strength and less than average human hand stability to open and close enabling a fast, simple, and easy to complete disconnection and connection respectively.

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

Although the invention has been explained in relation to various embodiments, it is to be understood that many other possible modifications and variations can be made without departing from the spirit and scope of the invention.

The invention claimed is:

1. A hand held catheter tubing grip shell for securing an operable catheter to catheter bag connection comprising
   a cylindrical clam shell having an interior and a hinge along a first longitudinal edge comprising
      a top half shell comprising a first semi-circular opening in a first end opposing a second semi-circular opening in a second end having a top thumb-lock rail along a second longitudinal edge opposite said first longitudinal edge,
      a bottom half shell comprising a third semi-circular opening in a third end opposing a fourth semi-circular opening in a fourth end having a bottom thumb-lock rail along a third longitudinal edge opposite said first longitudinal edge aligned to mate with said top thumb-lock rail,
      a compressible lining covering said interior of said cylindrical clam shell, and
      a thumb-lock tab for a locking of said cylindrical clam shell having a knurled surface for sliding over said top thumb-lock rail and said bottom thumb-lock rail.

2. The hand held catheter tubing grip shell of claim 1 wherein said cylindrical clam shell further comprises a length that is between six and eight centimeters.

3. The hand held catheter tubing grip shell of claim 1 wherein said first semi-circular opening, said second semi-circular opening, said third semi-circular opening, and said fourth semi-circular opening further comprises a diameter that is between one and three centimeters.

4. The hand held catheter tubing grip shell of claim 1 wherein said thumb-lock tab further comprises a knurled edge.

5. The hand held catheter tubing grip shell of claim 1 further comprising a closing of said cylindrical clam shell wherein a resistance to closing is less than three kilograms.

6. The hand held catheter tubing grip shell of claim 1 wherein said locking further comprises a force to close of less than one kilogram to move said thumb-lock tab.

\* \* \* \* \*